United States Patent [19]
Lilley

[11] Patent Number: 5,879,406
[45] Date of Patent: Mar. 9, 1999

[54] ARTIFICIAL JOINT BIOPROSTHESIS FOR MITIGATION OF WEAR

[75] Inventor: Edward Lilley, Shrewsbury, Mass.

[73] Assignee: Saint-Gobain Industrial Ceramics, Inc., Worcester, Mass.

[21] Appl. No.: 893,278

[22] Filed: Jul. 15, 1997

[51] Int. Cl.$^6$ ............................................. A61F 2/32
[52] U.S. Cl. ............................................................ 623/22
[58] Field of Search .............................. 623/18, 20, 21, 623/22, 23

[56] References Cited

U.S. PATENT DOCUMENTS

| | | | |
|---|---|---|---|
| 3,864,758 | 2/1975 | Yakich | 623/22 |
| 4,031,570 | 6/1977 | Frey | 623/22 |
| 4,571,358 | 2/1986 | Suh et al. | 428/155 |
| 4,731,088 | 3/1988 | Collier | 623/22 |
| 4,822,368 | 4/1989 | Collier | 623/22 |
| 5,152,794 | 10/1992 | Davidson | 623/18 X |
| 5,378,228 | 1/1995 | Schmalzried et al. | 604/8 |
| 5,514,182 | 5/1996 | Shea | 623/18 |
| 5,514,184 | 5/1996 | Doi et al. | 623/23 |
| 5,549,697 | 8/1996 | Caldarise | 623/18 X |
| 5,549,699 | 8/1996 | MacMahon et al. | 623/22 |
| 5,571,195 | 11/1996 | Johnson | 623/23 X |
| 5,641,323 | 6/1997 | Caldarise | 623/18 X |
| 5,702,483 | 12/1997 | Kwong | 623/23 |

FOREIGN PATENT DOCUMENTS

| | | |
|---|---|---|
| 346294 | 12/1989 | European Pat. Off. . |
| 2242065 | 4/1974 | France . |
| 2 537 868 | 6/1984 | France ..................................... 623/22 |
| 1 127 584 | 12/1984 | U.S.S.R. ................................. 623/22 |
| 2191402 | 12/1987 | United Kingdom . |

OTHER PUBLICATIONS

Tanchuling Jr., Antonio et al, "Does Reverse Hybrid Total Hip Arthroplasty Cause Lower Wear Rate and Osteolysis?", AAOS, 1997.

Khalily, C. et al, "Effect of Locking Mechanism on Particle and Fluid Migration Through Modular Acetabular Components", 64th Annual Meeting of the American Academy of Orthopaedic Surgeons, Feb. 13–17, 1997.

Reflection I & FSO Porous–Coated Acetabular Component Surgical Technique, Technique Described by John M. Cuckler, M.D., pp. 1–16.

*Primary Examiner*—Mary Beth Jones
*Attorney, Agent, or Firm*—Thomas M. DiMauro

[57] ABSTRACT

This invention relates to an acetabular cup having a substantially hemispherical ceramic concave surface comprising at least one debris reservoir thereon having a width of between 0.010 mm and 2 mm, and also to a ceramic hip joint prosthesis head whose outer surface comprises a similar debris reservoir.

20 Claims, 6 Drawing Sheets

ARTIFICIAL JOINT BIOPROSTHESIS FOR MITIGATION OF WEAR

BACKGROUND OF THE INVENTION

One of the most challenging problems in the field of artificial hip joints is the wear debris caused by articulation between the surfaces of the polyethylene acetabular cup and the metal or ceramic hip joint head. Even at a low wear rate such as 0.1 mm per year, the debris resulting from this wear is considered to be significant because it enters the vascular system of the human body and may cause osteolysis.

Some investigators have proposed reducing the wear problem by a variety of different methods. For example, U.S. Pat. No. 5,378,228 ("Schmalzried") suggests surrounding the prosthetic device with a series of funnels and reservoirs. U.S. Pat. No. 5,514,184 ("Doi") suggests providing a protector along the outer edge of the cup to catch debris. U.S. Pat. No. 4,822,368 ("Collier"), EPO Published Application No. 0 346 294 ("Impallomeni"), and U.S. Pat. No. 5,514,182 ("Shea") each suggest surrounding at least one of the articulation surfaces with a semi-permeable membrane which permits fluid circulation but traps debris. However, each of these systems adds greatly to the complexity of the prosthesis.

Therefore, there is a need for a simple bioprosthetic system which reduces the danger caused by articulation-induced wear.

SUMMARY OF THE INVENTION

In accordance with the present invention, there is provided a joint bioprosthesis comprising:

i) a material suitable for implantation within a human body, ii) a first surface having a shape suitable for fixation, and iii) a second surface having a shape suitable for joint articulation, wherein the second surface comprises at least one debris reservoir thereon.

In some embodiments, at least a portion of the second surface has a surface roughness $R_a$ of no more than 50 nm. In other embodiments, the debris reservoir has a width of between 0.010 mm and 2 mm. In preferred embodiments, the second surface is either i) substantially spherical (for use as a hip joint head), ii) concave and substantially hemispherical (for use as a hip joint cup), or iii) has a shape suitable for articulation with a third surface selected from the group consisting of a tibial knee joint surface and a femoral knee joint surface. In some embodiments, the first surface is either a frustoconical recess (for fixation to a hip trunnion), or has a shape suitable for fixation with an acetabulum. In some embodiments, the material is preferably a biomedical grade ceramic, and more preferably a biomedical grade zirconia.

Also in accordance with the present invention, there is provided a hip joint prosthesis head comprising:

a) a substantially spherical outer surface having a diameter of between 15 mm and 50 mm, and b) a tapered recess extending inward from the outer surface, the recess having an outer diameter of at least 4 mm and a depth of at least 6 mm, wherein the outer surface comprises at least one debris reservoir thereon having a width of between 0.010 mm and 2 mm.

Also in accordance with the present invention, there is provided an acetabular cup having a substantially hemispherical concave surface preferably having a maximum diameter of between 15 mm and 50 mm, the concave surface comprising a material selected from the group consisting of a metal, a polymer and a ceramic, and further comprising at least one debris reservoir thereon having a width of between 0.010 mm and 2 mm.

Also in accordance with the present invention, there is provided a femoral prosthesis comprising:

a) a substantially spherical hip joint prosthesis head having an outer surface, and b) an acetabular cup having a concave surface, the concave surface having a shape substantially corresponding to the outer surface of the head, wherein the head outer surface and the concave surface of the cup are positioned to substantially contact and articulate with each other to define an articulation interface, and wherein at least one of the outer surface of the head and the recessed surface of the cup comprises at least one debris reservoir thereon.

DETAILED DESCRIPTION OF THE INVENTION

Figure 1:
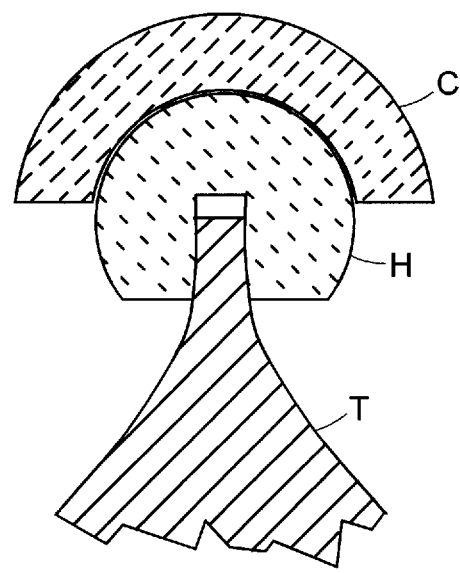
FIG. 1 is a cross section of a conventional hip joint prosthesis comprising a smooth surfaced head H, a trunnion T and a smooth surfaced cup, wherein the head H is attached to the trunnion T and its outer surface articulates with the concave surface of cup C.

The problems caused by wear debris in a hip joint prosthesis can be at least partially solved by providing at least one of the articulation surfaces thereof with at least one debris reservoir thereon. This debris reservoir will act as a receptacle for collecting debris generated at the articulation interface, thereby preventing the debris from leaving the prosthesis area and entering the vascular system. Since the body's macrophages typically do not have access to the sliding interface, the presence of the debris in the grooves will not trigger an adverse reaction and so will not cause harm to the body. In addition, removal of the debris by the debris reservoir also acts to clean the articulation interface, thereby preventing exacerbation of debris-induced wear at the interface.

Preferably, the joint is a hip joint comprising a hip joint head which articulates with a hip joint cup. Referring now to the substantially spherical hip joint prosthesis head 10 provided in FIG. 2a, the debris reservoir can assume any recessed shape, including continuous channels 1, longitudinal rings 2a and 2b around the spherical surface, isolated channels such as hemispherical holes 5a, square holes 5b, grooves 6 radially extending from a center hole 7, or reservoir 8 placed in fluid connection with an inner void region 9 via channel 21. Preferably, the reservoirs are longitudinal rings. These reservoirs can also be advantageously used within the concave surface of the acetabular cup as well, as shown by the groove 16 in FIG. 3.

Figure 2A:
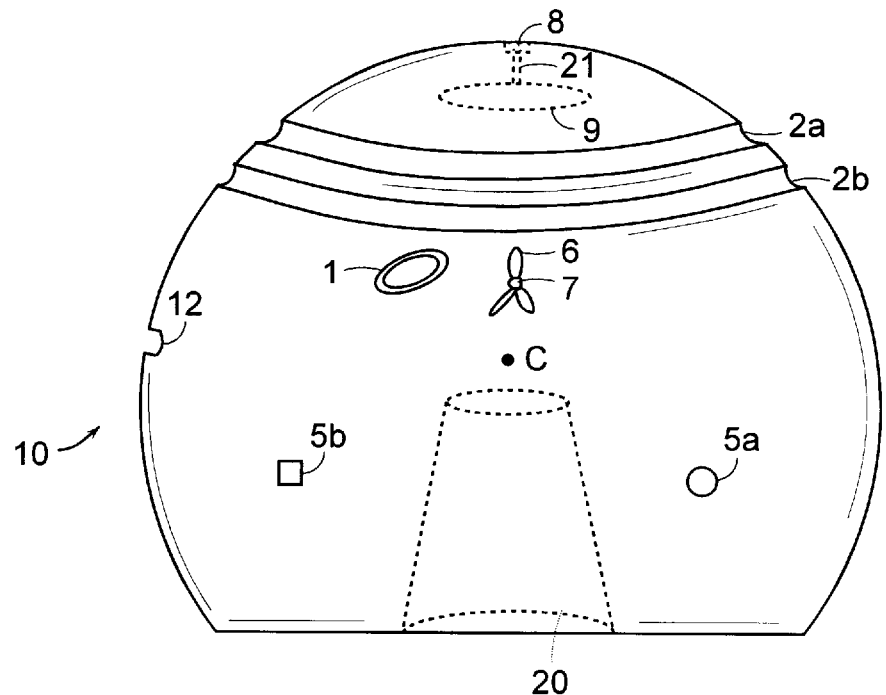
FIGS. 2a and 2b are perspective views of substantially spherical hip joint prosthesis heads having debris reservoirs upon their outer surfaces.

When provided on the surface of the conventional hip joint prosthesis, the dimensions of the debris reservoir are much smaller than those of the larger tapered recess 20 (shown in FIG. 2a). The tapered recess is commonly provided for tapered locking with a femoral trunnion and is typically at least 4 mm in outer diameter and at least 6 mm in depth.

Figure 2B:
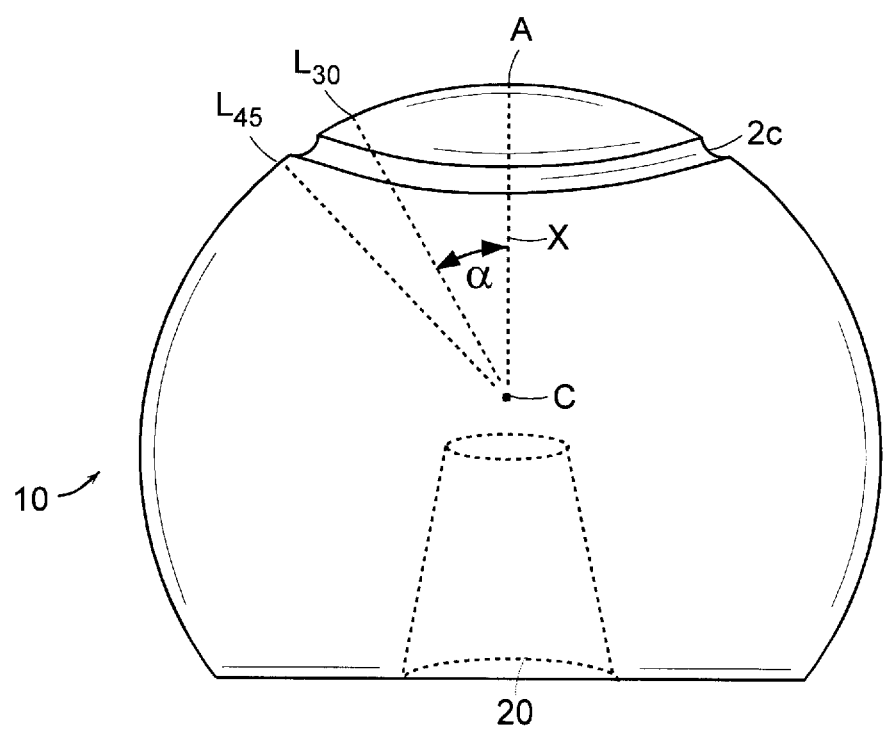
Figure 3:
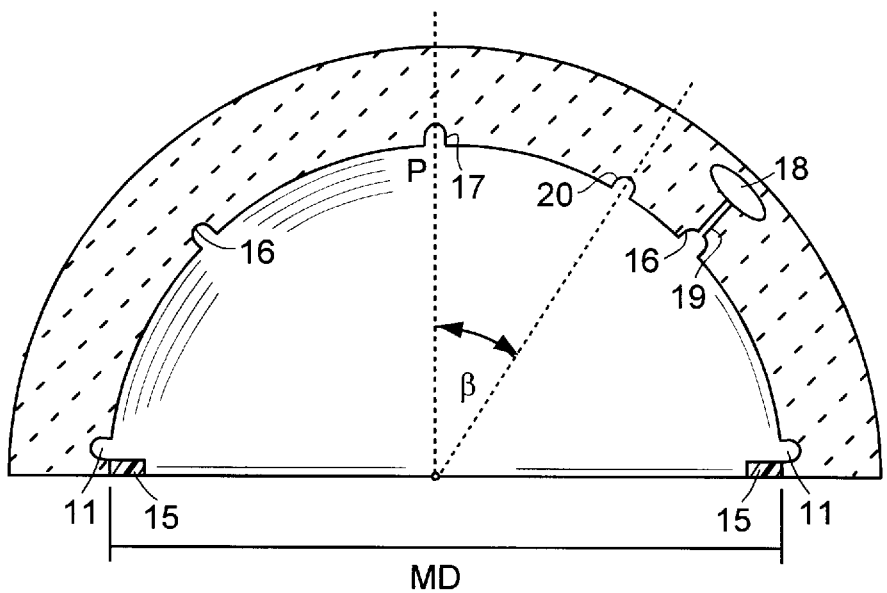
FIG. 3 is a cross sectional view of an acetabular cup having a plurality of debris reservoirs upon its concave surface.

In some general embodiments of the present invention, the reservoirs are provided as rings substantially centered about either the apex of the head or the centerpoint of the cup's concave surface. In particular, in head-based embodiments, the head has an internal centerpoint C (as shown in FIG. 2b), wherein the outer surface of the head defines an apex A located substantially opposite the tapered recess 20 and an axis X connecting the apex and the centerpoint, and wherein at least one debris reservoir 2c is provided on the outer surface at a position which defines a line L between the centerpoint C and the position of the debris reservoir, the line L and the axis X defining an intersection at the centerpoint C, wherein the intersection of the axis X and the line L defines an angle α which is typically between 10 and 60 degrees (and preferably is between 30 and 45 degrees). Lines $L_{30}$ and $L_{45}$ in FIG. 2b represent lines whose intersection with axis X produce angles α of 30 and 45 degrees, respectively, while debris reservoir 2c lies within the angle 30°<α<45°. In cup-based embodiments, and referring now to FIG. 3, the cup's concave surface has i) a centerpoint P, and ii) a maximum diameter MD defining an equator, the centerpoint P and the equator positioned along the substantially hemispherical surface at an angle β of 0 degrees and 90 degrees respectively, and at least one debris reservoir is provided at a position defining an angle β of between 10 and 60 degrees (preferably between about 30 and 45 degrees). In FIG. 3, reservoirs 20 and 16 are located at positions of about 30 and 45 degrees, respectively. Because these embodiments possess symmetry about the apex/centerpoint of the prosthetic component, they do not require extra care on the part of the surgeon to specifically orient them during surgery.

When the head outer surface is ceramic, the corresponding concave surface of the cup will be either ceramic or polymer. As the type, amount and effect of debris produced by articulation in a polymer cup-containing prosthesis is different than that produced by a ceramic cup-containing prosthesis, the purpose of the debris reservoir should also change. Accordingly, in more preferred embodiments, desirable selection of the debris reservoir's dimensions, location and position will vary depending upon whether the cup's concave surface is ceramic or polymer.

The positions of the reservoirs upon the articulation surface should be selected in accordance with the predetermined area of maximum wear upon the articulation surface. Once implanted, the orientation of the cup relative to the human acetabulum is such that the maximum load upon either articulation surface occurs at an angle γ (typically, between about 30° and 45°, and most typically is about 37°) from each of the centerpoint P of the cup's concave surface and the apex A of the head (as shown by point ML and angle γ in FIG. 5). In particular, whereas the articulation surfaces positioned near point ML experience about 100 psi load, the surfaces near the equatorial regions C and D of the cup's concave surface and the head may experience much lower loads. Since a region having an increased normal loading likely has increased wear, positioning of the reservoirs should reflect concern for this area of increased wear.

When the cup has a polymer concave surface (such as polyethylene), a relatively large amount of debris (most of which is polymer) should be expected. As polymer debris is considered to be dangerous to the body in the expected quantities, this debris should not be allowed to leave the prosthesis. Accordingly, the reservoirs in prostheses having polymer cups should be designed to effectively retain any debris generated at the articulation interface.

Figure 4:
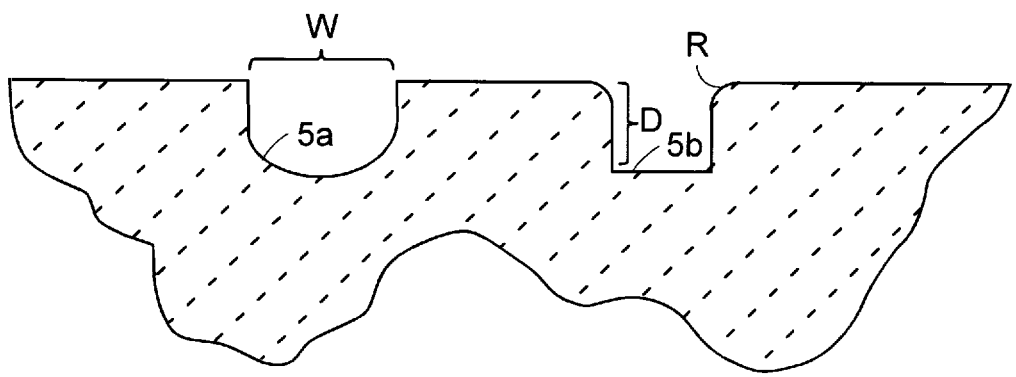
FIG. 4 is a cross sectional view of an articulation surface having debris reservoirs thereon.

The dimensions of the debris reservoirs in a prosthesis having a polymer cup should be sufficiently large to retain the large amount of polymer debris expected to be generated over the life of the prosthesis. Reference is now made to FIG. 4, which presents debris reservoirs as grooves 5a and 5b formed in articulation surface 30. Each debris reservoir has a depth D and a width W. For a polymer cup containing-prosthesis, these reservoirs should be large, that is, between about 0.5 and 2 mm wide (W), preferably between about 0.5 and 1 mm in width. If the reservoir is narrower than 0.5 mm in width, it may have insufficient storage volume for retaining the expected volume of polymer debris particles. If the reservoir is wider than 2 mm, then local stresses may result. Similarly, the depth of a reservoir in a prosthesis having a polymer cup is also large, preferably between about 0.5 and 5 mm deep (D), more preferably between 1 mm and 2 mm. If the reservoir is less than about 0.5 mm deep, it likely has insufficient storage volume for retaining the expected volume of polymer debris particles. In some polymer cup embodiments, the reservoirs are about 1 mm wide and about 1 mm deep.

Generally, the debris reservoirs in a polymer cup-containing prosthesis may be located on either the cup or head articulation surface. For example, reservoirs may be provided on the head outer surface essentially opposite the recess (i.e., at the apex of the head), as shown by reservoir 8 and longitudinal rings 2a and 2b of FIG. 2a. Preferably, the debris reservoirs are positioned anywhere on either articulation surface which remains in constant contact with its corresponding articulation surface. As the wide range of motion in normal articulation frequently results in nearly every portion of the head surface being out of the articulation interface for some significant period of time (thereby allowing the retained-but-dangerous polymer debris to exit the prosthesis), the reservoirs in a polymer cup-containing prosthesis are more preferably located on the cup's concave surface.

Figure 5:
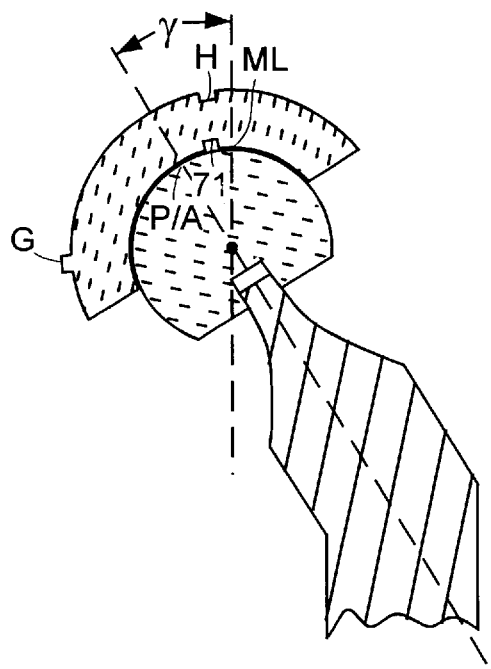
FIG. 5 is a cross-section of a hip joint prosthesis which identifies the point of maximum loading ML.

The "point of maximum load" as used herein to define the position of a reservoir on a cup's concave surface varies from cup design to cup design, but is typically an easily identifiable region within any cup. Simply, it is the point on the concave surface at which the concave surface, when in-place in an upright human, is normal to the vertical plane. Because it bears a substantially normal load, this surface will experience the highest wear of any portion of the concave surface of the cup. This point can be easily identified after use in in vivo or hip joint simulator tests, as it is in the middle of the area having the most scratches, and this area typically spans about 20 degrees in every direction from the point of maximum load. However, the point of maximum load can also be identified by the shape of a cup's backing portion. Typically, a cup backing is not designed with 360 degree symmetry, but rather includes asymmetrically-placed backing components such as pegs and holes for fitting into the acetabulum in a desired, predetermined angle of orientation. This angle of orientation (as defined by backing pegs G and holes H, as shown in FIG. 5) allows the point of maximum load to be easily identified, thereby also defining the area of maximum wear on the cup's concave surface. Typically, the positions of the point of maximum load ML and the cup centerpoint P define an angle of maximum load $\gamma$, as shown in FIG. 5, which is between about 10 and 60 degrees, preferably between 30 and 45 degrees.

In one embodiment, as shown in FIG. 5, the debris reservoir 71 is located at the point of maximum load ML. The advantage of locating a debris reservoir at this point is that this position provides the greatest opportunity for quickly trapping polymer debris as it is generated. However, as the reservoir is located in the region of highest polymer wear, there is also a great danger that the depth of the reservoir will be reduced over time (e.g., lose about 1 mm in depth over about 10 years), thereby freeing the polymer debris it has trapped over the years. This wear problem could be mitigated by providing a deep hole in fluid connection with an inner void, as shown in FIG. 3. However, this mitigation adds to the complexity of the design. Moreover, even if the wear problem was so managed, the reservoir (which is preferably no more than 2 mm wide) is still essentially only a point sink, and so is not very effective in trapping all the debris being generated everywhere on the articulation interface, though mostly at the area of maximum wear.

Figure 6:
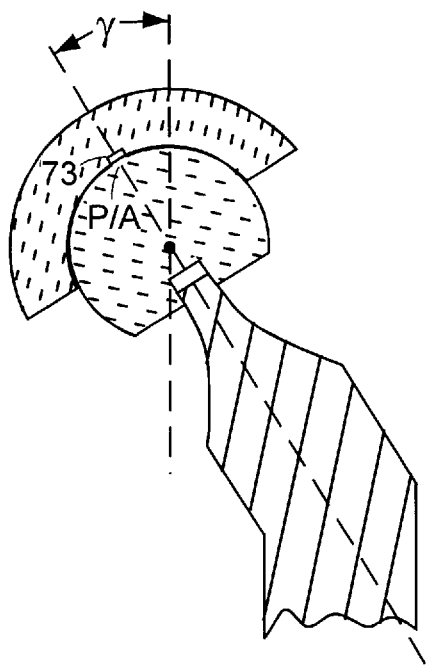
FIG. 6 is a cross-section of a hip joint prosthesis which identifies a debris reservoir 73 located substantially near the centerpoint of the concave surface of the acetabular cup.

Therefore, in one preferred embodiment, shown in FIG. 6, the debris reservoir 73 is located substantially near the centerpoint P of the concave surface, as is hole 17 of FIG. 3. Another advantage of locating the debris reservoir at the centerpoint of the cup is that this location provides the least opportunity for debris to escape the articulation interface. However, as this reservoir is restricted to essentially a single point, it also is not very effective in trapping all the generated polymer debris.

Figure 7:
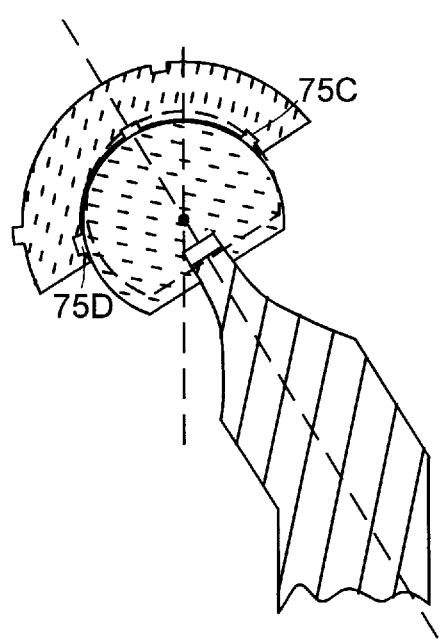
FIG. 7 is a cross-section of a hip joint prosthesis which identifies debris reservoir 75C and 75D located substantially near the equatorial region of the concave surface of the acetabular cup.
Figure 8:
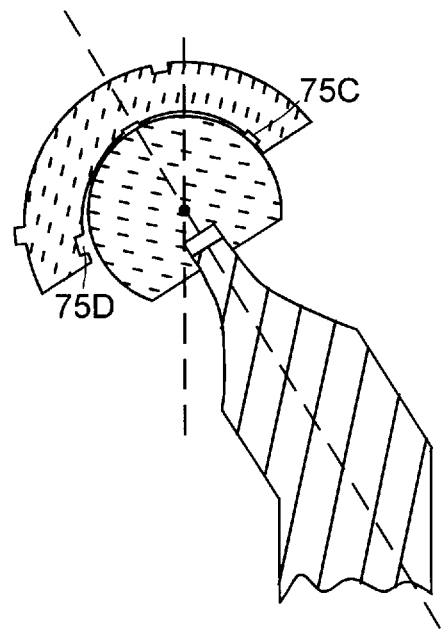
FIG. 8 is a cross-section of a hip joint prosthesis wherein a gap develops between the head and cup.

In a second preferred embodiment, shown in FIG. 7, a reservoir 75C and 75D substantially traverses near the equatorial region of the concave surface of the acetabular cup (i.e., near the recessed surface's maximum diameter, also as shown by reservoir 11 in FIG. 3). However, these equatorial reservoirs should not be so large and so near the cup's edge that the material near the edge of the cup flexes (i.e., the edge of the cup should be rigid). By placing the debris reservoir 75C and 75D as far away from the point of maximum load ML as possible, the problem of erosion is minimized. In addition, the large ring which is the reservoir 75C and 75D provides a much larger debris-retention capacity than the point sinks of FIGS. 5 and 6. However, it also is known that, during service, the continual normal loading of the head against the slightly-tilted polymer cup concave surface tends to asymmetrically deform the cup surface to a shape shown by the dotted line in FIG. 7. In this condition, the head moves further into the cup than desired and there is a danger that a gap will develop between the head surface and the cup surface located near the portion of the reservoir at 75D, thereby freeing the debris reservoir from the articulation interface and allowing polymer debris trapped therein to enter the body, as shown in FIG. 8. (Although the cup surface may also deform at point C, that deformed region may nonetheless continue to contact the head surface and the debris therein may remain trapped.) In addition, since the reservoir section located at 75C is closer to the area of maximum wear, there is a danger that it will trap debris faster than the portion of the reservoir at 75D, and so overflow quicker.

Figure 9:
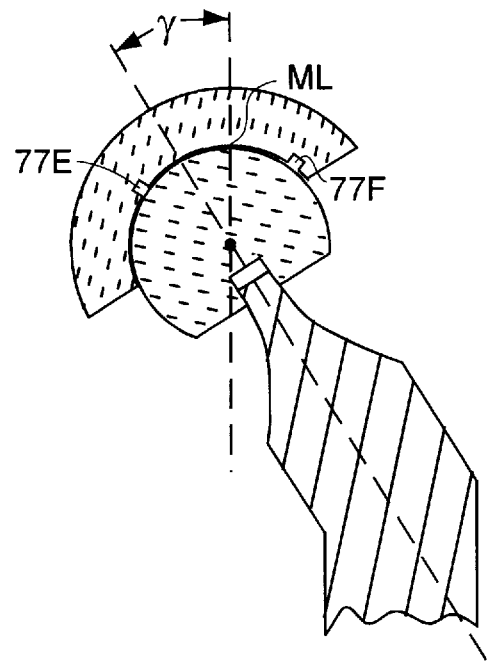
FIG. 9 is a cross-section of a hip joint prosthesis wherein reservoir 77E and 77F is located substantially about the point of maximum loading ML.

Therefore, in a third preferred embodiment, the problems of low trapping volume, reservoir erosion, non-uniform trapping and cup deformation are mitigated by providing at least one reservoir 77E and 77F as a ring substantially about the point of maximum load ML, as shown in FIG. 9. Because this reservoir is located relatively far away from the point of maximum load ML, the danger of wearing away its walls is reduced. Because the reservoir at point 77E is located relatively far away from the equatorial region (as compared to 75D of FIG. 7), it will still contact the head surface after deformation, and not release debris. In addition, as the reservoir 77 is located essentially concentrically about the point of maximum load ML, the debris will more likely enter the reservoir 77E and 77F at a substantially more spatially uniform rate.

When the cup concave surface and the head outer surface are each ceramic, not only it is expected that ceramic-ceramic sliding will produce much less debris (and so lessen the need for high volume reservoirs), but also the ceramic debris produced is relatively bioinert and therefore much less dangerous to the body. Accordingly, the need for the reservoirs in a ceramic/ceramic coupling to retain large amounts of debris are substantially lessened. However, the same ceramic debris is much more dangerous to the highly polished ceramic sliding surfaces than polyethylene debris. Investigation of the effect of ceramic debris on polished ceramic sliding surfaces has shown that the ceramic debris tends to stick to one of the ceramic sliding surfaces and become mini-grinding wheels, thereby accelerating wear. Although lubrication may help remove this stuck debris, there may be occasions in the lifetime of the hip joint prosthesis when the surface has insufficient lubrication for this purpose. Therefore, in these situations, the function of the reservoirs is primarily that of removing the dangerous ceramic debris from the polished sliding surfaces as quickly as possible.

As the need for retaining large amounts of debris is lessened in the ceramic-ceramic coupling, the volume of the reservoirs is correspondingly lessened. Accordingly, referring again to the reservoir dimensions of FIG. 4, when the cup and head are each ceramic, the reservoirs are preferably between about 0.010 mm and 0.100 mm, preferably between about 0.020 mm and 0.050 mm in depth. Similarly, the reservoirs are preferably between about 0.010 mm and 0.100 mm, preferably between about 0.020 mm and 0.050 mm in width. These smaller reservoirs have the advantage that they will likely be much less deleterious to the strength of the cup or head surface upon which they are placed. In addition, in these ceramic-ceramic couplings, the reservoir preferably has rounded edges R to mitigate catastrophic damage.

When the cup and head are each ceramic, the volume of debris expected to be generated is much smaller, and its effects are much less of a concern, and so there is no critical need to prevent the debris from exiting the prosthesis. In light of this lessened need, the location of the reservoirs need not be so restricted. Accordingly, the reservoirs in ceramic-ceramic couplings can be suitably located upon the head surface as well as the cup surface, even if their location on the head surface periodically becomes free of the articulation interface.

As noted above, when the head and cup are each ceramic, the function of the reservoir is primarily that of removing the dangerous ceramic debris from the polished sliding surfaces as quickly as possible. Accordingly, the reservoirs should be positioned to provide quick removal of the wear-accelerating ceramic debris.

Figure 10:
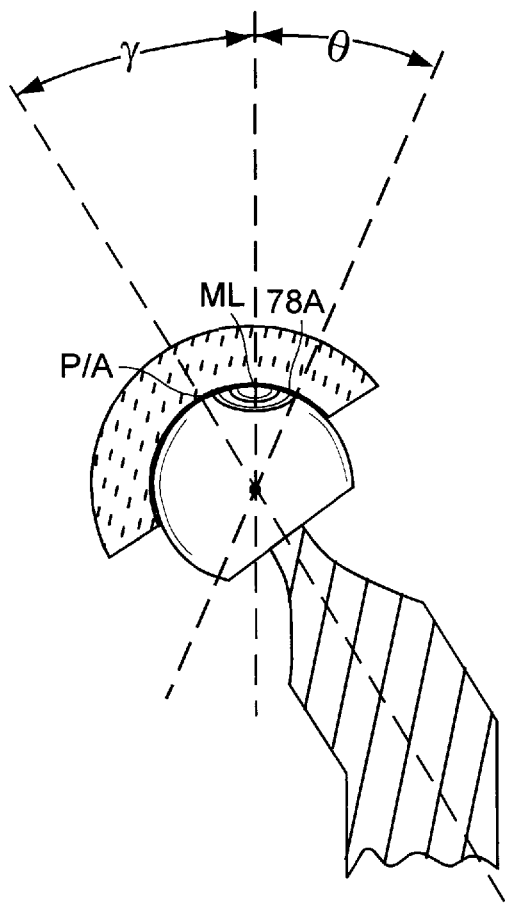
FIG. 10 is a cross-section of a hip joint prosthesis wherein reservoir 78a is shaped as a circle having a midpoint at the point of maximum loading ML.

In one embodiment, a reservoir is positioned (on either articulation surface) as a ring about the line of maximum load. Since the amount of debris is expected to be small, both the erosion of the reservoir and the volume of debris are likewise small, and so reservoir overflow is not a concern. Preferably, the reservoir 78a is shaped as a circle having an midpoint at the point of maximum loading ML, as shown on the had in FIG. 10. On either articulation surface, the circular reservoir is generally centered about a point distanced from either the head apex A or the cup centerpoint P by an angle τ of between 10 and 60 degrees, preferably between 30 and 45 degrees, more preferably about 370° in order to remove the ceramic debris from the sites of its most rapid generation as quickly as possible. More preferably, the circular reservoir has a radius which defines an angle θ of no more than about 20° relative to the point of maximum load ML. In some embodiments, there are a plurality of debris reservoirs 78a and 78b, each positioned concentrically about the point of maximum loading ML, preferably each defining an angle θ of no more than about 20°.

In general, when the head outer surface is metallic, the corresponding concave surface of the cup will be either metal or polymer.

The acetabular cup can be made of any material commonly used for an acetabular cup, including polymers, metals and biomedical grade ceramics. If a polymer is selected, then polyethylene is preferred. If metals are selected, chrome-cobalt and titanium alloys are preferred. If ceramics are selected, the cup may comprise alumina, zirconia or mixtures thereof. In some embodiments, the cup can be made of yttria tetragonal zirconia polycrystal (YTZP) ceramic. In others, at least the concave surface of the cup is made of fine grained (less than 2 um) alumina. Typically, the cup's concave surface has a diameter of between 15 mm and 50 mm (preferably between 22 mm and 32 mm), and a surface roughness Ra of no more than 50 nm, preferably no more than 10 nm. Preferably, the cup has a density of at least 99% of theoretical density.

In embodiments related to the hip joint prosthesis, the head of the present invention can be made of any material commonly used as a head in a hip joint prosthetic, including metals and obiomedical grade ceramics. If ceramics are selected, the cup may comprise alumina, zirconia or mixtures thereof. In some embodiments, the cup can be made of yttria tetragonal zirconia polycrystal (YTZP) ceramic. Typically, the head's outer surface has a diameter of between 15 mm and 50 mm (preferably between 22 mm and 32 mm), and a surface roughness Ra of no more than 10 nm, preferably no more than 5 nm. Preferably, the head has a density of at least 99% of theoretical density, and its tapered recess has a total angle of between 4° and 10°, preferably about 6°.

When a zirconia is selected for use as an articulation surface, it preferably consists essentially of a biomedical grade zirconia ceramic comprising at least about 90 mol % zirconia, and more preferably is a partially stabilized zirconia (PSZ) which contains at least about 90% tetragonal zirconia. The PSZ is typically partially stabilized by a rare earth oxide (which includes yttria) at a concentration of between about 2 mol % and about 5 mol %. Most preferably, the PSZ is yttria stabilized tetragonal zirconia polycrystal (YTZP). Preferably, the YTZP has a mean grain size (SEM using ASTM E 112/82) of no more than 1 micron (um), preferably between 0.3 and 0.8 um. The bulk of the head should have a four point flexural strength of at least about 920 MPa, preferably at least 1300 MPa. Its density should be at least 99.7% of theoretical density, preferably at least 99.8%. In some embodiments, it has an elasticity modulus of no more than 220 GPa; an open porosity of no more than 0.1%; less than 1% impurities; and a fracture toughness (as per Chantikul) of at least 5 MPa m$^{1/2}$.

In one preferred method of making the YTZP zirconia, the rare earth oxide powder is co-precipitated with zirconia powder to produce a powder which is cold isostatically pressed at between 50 and 400 MPa and appropriately green machined to form a green sphere which is then sintered at between about 1300° C. and 1500° C. for about 1 to 4 hours to achieve a density of at least 95%; and the sintered piece is hipped in an inert gas such as argon at between 1300° C. and 1500° C. for between 0.5 and 4 hours to produce a sintered sphere having a density of at least 99.9%, and a grain size of less than one micron.

If alumina is selected as the ceramic, it preferably has a grain size of less than two microns, preferably less than one micron (by linear intercept method). Preferably, this alumina ceramic has a density of at least 3.9 g/cc, more preferably at least 3.97 g/cc; and a grain size of between 1 and 2 um. In some embodiments, it has a 4 point flexural strength of at least 400 MPa, more preferably at least 550 MPa. A preferred alumina can be produced by sintering biomedical grade alumina at about 1300°–1500° C. for about 60 minutes and then hipping at 1300°–1500° C. and 200 MPa for 60 minutes. In addition, sol gel processes such as those disclosed in U.S. Ser. No. 07/884,817, now abandoned, or U.S. Pat. No. 4,657,754, the specifications of which are incorporated by reference, can also be used to make fine grained alumina.

Preferably, each articulation surface has a surface roughness Ra which is as low as possible. If either a ceramic cup or a ceramic head is used, the articulating surface thereon may be polished to the desired surface roughness Ra in accordance with U.S. Ser. Nos. 08/609,711 and/or 08/521,152, the specifications of which are incorporated by reference herein. Preferably, the surface roughness Ra for such ceramic surfaces is no more than 50 nm, more preferably no more than 10 nm.

Figure 11:
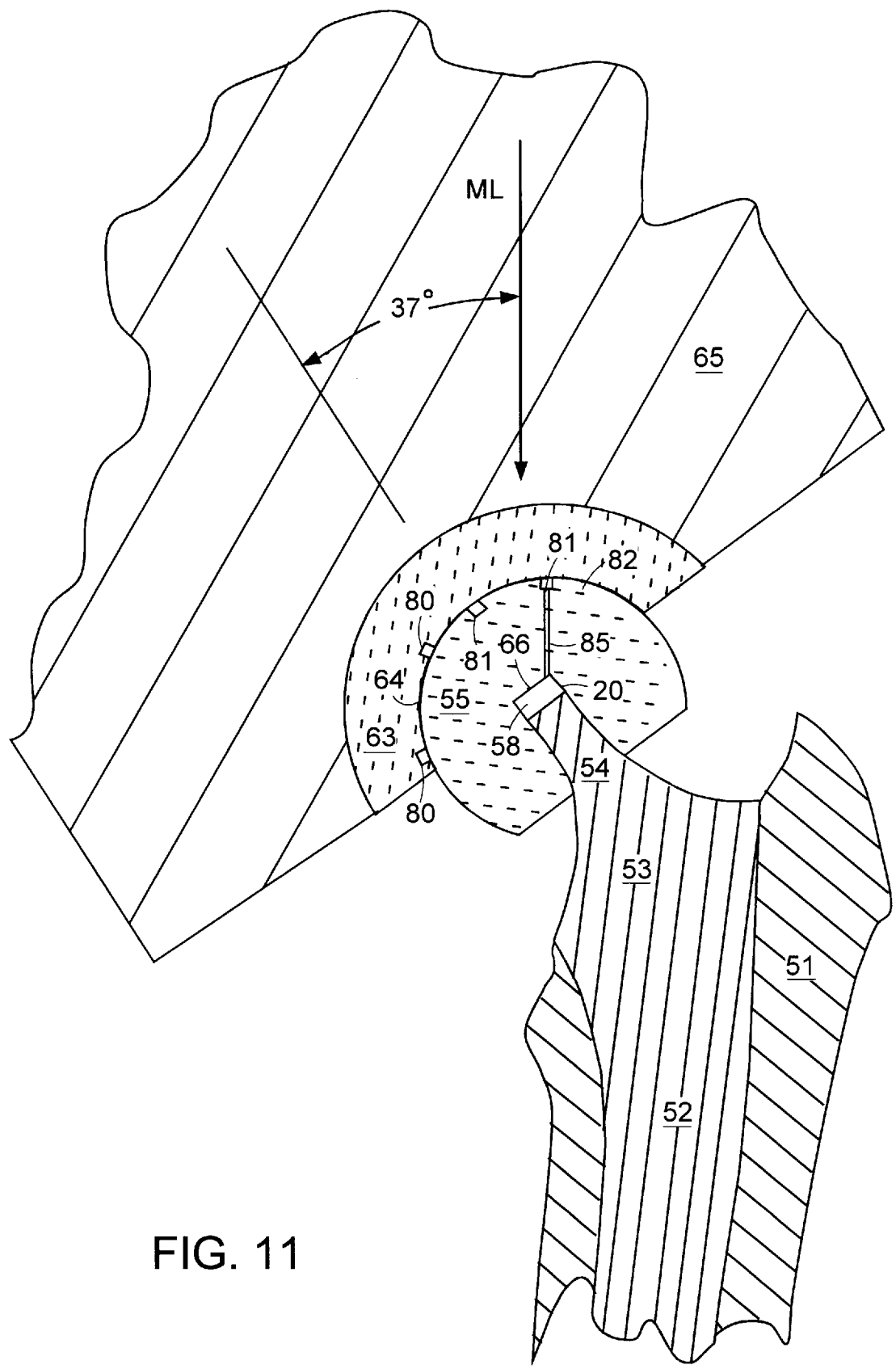
FIG. 11 is a cross sectional view of a hip joint prosthesis of the present invention comprising a head whose substantially spherical surface has debris reservoirs thereon, and an acetabular cup whose concave surface has debris reservoirs thereon.

In use, and referring now to FIG. 11, in one embodiment, there is provided a femoral prosthesis according to the present invention comprising:

a) a substantially spherical hip joint prosthesis head having an outer surface, and b) an acetabular cup having a concave surface, the concave surface having a shape substantially corresponding to the outer surface of the head, wherein the head outer surface and the concave surface of the cup are positioned to substantially contact and articulate with each other to define an articulation surface, and wherein at least one of the outer surface of the head and the concave surface of the cup comprises at least one debris reservoir thereon within the articulation surface.

The first end 53 of metal trunnion 52 is implanted into femur 51. The second end of the trunnion 52 is shaped to a frustocone 54. The outer surface 82 of the head 55 has debris reservoirs 81 thereon. The recess 20 of the zirconia head 55 has about the same tape angle as cone 54, and is press fit onto cone 54. A reserve 58 between the frustocone 54 and the crown 66 is also shown. Concurrently, an acetabular cup 63 having a concave surface 64 for receiving the head 55 is fitted into the pelvic bone 65. Concave surface 64 further comprises debris reservoirs 80 for receiving debris. The head 55 is positioned in the concave surface 64 of the acetabular cup 63 to form the hip joint. When the hip pivots and the articulation surfaces move relative to each other, debris particles are generated at the articulation interface, predominantly near the apex of the cup. These particles will be swept by the motion of the spherical head and fall into the debris reservoirs 80 and 81 which will retain them. If synovial fluid is present within the sliding interface, the sweeping of the debris particles will be further enhanced.

In other embodiments of the invention, the acetabular cup's concave surface is provided with a lip action 15, as shown in FIG. 3. During articulation, this lip wipes the surface of the femoral head and sweeps the interfacial debris into the reservoirs. A lip is typically created by attaching a second material such as a plastic to the cup. The second material should have superior wiping properties, including durability and flexibility. It typically has a length of about 2 mm.

Although keeping the width and depth of the grooves small has certain mechanical advantages, such small grooves will likely more quickly fill up and may overflow with debris, and the prosthesis will thereby lose the advantage of debris having been removed from its sliding surface. In some embodiments of the present invention, the potential overflow problem is solved by providing a narrow internal channel which provides fluid connection between the debris reservoirs at the surface of the prosthetic component with a more remote reservoir (or inner void) within the component. This is demonstrated in a head by channel 8, cylindrical hole 21, and inner void 9 in FIG. 2a. It is also shown in the cup of FIG. 3 by channel 19 providing fluid connection between reservoir 16 and inner void 18. This narrow channel allows the debris to drain from the surface grooves to a more secure reservoir, and thereby replenishes the debris-carrying capacity of the reservoirs at the component surface.

As shown in FIG. 11, in one embodiment, the remote reservoir is reserve 58 which is in fluid connection with debris reservoir 81 via channel 58. Therefore, in some embodiments, the at least one debris reservoir is provided on the head outer surface, the head recess defines a frustoconical surface, the head further comprises a channel in fluid connection with the at least one debris reservoir, and the prosthesis further comprises:

c) a trunnion having a tapered stem adapted for friction fitting with the tapered recess of the head, the tapered stem being substantially friction fitted into the tapered recess of the head, to form a reserve defined by the friction fit of the frustoconical surface of the head and the stem, wherein the channel provides fluid connection between the at least one debris reservoir and the reserve.

In one embodiment of the present invention which uses the separate reservoir concept, a small cylindrical hole is provided near the apex of the spherical head which extends all the way to the taper recess, and the void is formed by the reserve between the upper portion of the trunnion and the deepest portion of the taper recess. The variable motion of this hole across the polyethylene cup surface would allow it to collect debris from the area of maximum wear.

If desired, the channels can also be provided with filter membranes which would allow fluid to drain through while retaining the debris.

It is acknowledged by the art that there is a possibility that the articulation surfaces of the bioprosthetic component can become dry during use, with the result of increasing friction and wear. However, the grooves of the present invention can also trap and retain synovial fluid and thereby act as a source for lubrication of the sliding surface. In use, lubricant trapped in the grooves could be released into the articulation interface when the surfaces surrounding the grooves slightly wear. The released lubricant could prevent further wear by reducing the friction coefficient of the articulation surfaces. It is believed that the embodiments of the present invention in which the grooves are connected to interior reservoirs by channels would provide a satisfactory means for trapping and retaining the lubrication near the sliding interface.

The present invention can be advantageously used within any bioprosthetic device in which sliding wear (especially from articulation) is expected to occur. This includes the hip joint prosthetic, the knee prosthetic, and shoulder prosthetic. Preferably, however, the prosthetic is a hip joint prosthetic comprising an acetabular cup and a spherical head.

As mentioned above, the present invention can also be advantageously used in a knee joint application. Therefore, in accordance with the present invention, there is also provided a knee joint prosthesis comprising:

a) a femoral component having a base and a plurality of tynes extending therefrom in the same direction, and b) a tibial plate having a receiving surface shaped for receiving the tynes, wherein the receiving surface has at least debris reservoir thereon having a width of between 0.1 mm and 2 mm.

I claim:

1. A ceramic hip joint prosthesis head comprising:
a) a substantially spherical outer surface having a diameter of between 15 mm and 50 mm, and
b) a tapered recess extendng inward from the outer surface, the recess having an outer diameter of at least 4 mm and a depth of at least 6 mm
wherein the outer surface comprises at least on debris reservoir thereon having a width of between 0.010 mm and 2 mm.

2. The head of claim 1 wherein the ceramic is selected from the group consisting of alumina and zirconia, and mixtures thereof.

3. The head of claim 2 wherein the ceramic is zirconia.

4. The head of claim 1 wherein the debris reservoir has a width of between about 0.010 mm and 0.100 mm, and a depth of between about 0.01 mm and 0.1 mm.

5. The head of claim 1 having a centerpoint, wherein the outer surface of the head defines an apex located substantially opposite the recess and an axis connecting the apex and the centerpoint, and wherein at least one debris reservoir is provided on the outer surface substantially concentrically about the apex, the reservoir having a radius which defines a line between the centerpoint and the radius of the debris reservoir, the line and the axis defining an intersection at the centerpoint, wherein the intersection of the axis and the line defines an angle α of between 10 and 60 degrees.

6. The head of claim 1 wherein the debris reservoir is located substantially opposite the recess.

7. The head of claim 1 having a centerpoint, wherein the outer surface of the head defines an apex located substantially opposite the recess and an axis connecting the apex and the centerpoint, and wherein the at least one debris reservoir is provided on the outer surface substantially concentrically about a midpoint which defines a line between the centerpoint and the midpoint, the line and the axis defining an intersection at the centerpoint, wherein the intersection of the axis and the line defines an angle $\tau$ of between 10 and 60 degrees.

8. The head of claim 7 wherein the radius of the debris reservoir defines an angle $\theta$ of no more than about 20 degrees.

9. The head of claim 7 wherein the intersection of the axis and the line defines an angle $\tau$ of between 30 and 45 degrees.

10. The head of claim 1 further comprising i) an inner void and ii) a channel which provides fluid connection between the inner void and the at least one debris reservoir.

11. An acetabular cup having a substantially hemispherical ceramic concave surface having a maximum diameter of between 15 mm and 50 mm, and further comprising at least one debris reservoir on the concave surface having a width of between 0.010 mm and 2 mm.

12. The cup of claim 11 wherein the ceramic is selected from the group consisting of alumina and zirconia.

13. The cup of claim 11 wherein the debris reservoir has a width of between about 0.010 mm and 0.100 mm, and a depth of between 0.01 mm and 0.1 mm.

14. The cup of claim 11 further comprising a backing having a shape defining a point of maximum load upon the concave surface, and the concave surface is comprised of a ceramic, wherein the debris reservoir is a ring provided substantially concentrically about the point of maximum load.

15. The cup of claim 14 wherein the point of maximum load defines an angle $\tau$ of between 10 and 60 degrees.

16. The cup of claim 14 wherein the debris reservoir has a radius about the point of maximum load defining an angle $\theta$ of no more than 20 degrees.

17. The cup of claim 11 wherein the concave surface has i) a centerpoint, and ii) a maximum diameter defining an equator, the centerpoint and the equator each defining a position $\beta$ along the substantially hemispherical concave surface of 0 degrees and 90 degrees respectively, and wherein at least one debris reservoir is provided substantially concentrically about the centerpoint and has a radius extending to the position $\beta$, wherein $\beta$ is between about 10 and 60 degrees.

18. The cup of claim 11 wherein the concave surface has a centerpoint and at least one debris reservoir is located substantially near the centerpoint.

19. The cup of claim 11 further comprising i) an inner void and ii) a channel which provides fluid connection between the inner void and the at least one debris reservoir.

20. A femoral prosthesis comprising:
  a) a substantially spherical hip joint prosthesis head having an outer surface, and
  b) an acetabular cup having a concave surface, the concave surface having a shape substantially corresponding to the outer surface of the head,
    wherein the head outer surface and the concave surface of the cup are positioned to substantially contact and articulate with each other to define an articulation surface, and
    wherein at least one of the outer surface of the head and the concave surface of the cup comprises at least one debris reservoir thereon,
    wherein the at least one debris reservoir is provided on the head outer surface, wherein the head tapered recess defines a frustoconical surface, wherein the head further comprises a channel in fluid connection with the at least one debris reservoir, wherein the prosthesis further comprises:
  c) a trunnion having a tapered stem adapted for friction fitting with the tapered recess of the head, the tapered stem being substantially friction fitted into the tapered recess of the head, to form a reserve defined by the friction fit of the frustoconical surface of the head and the stem,
    and wherein the channel provides fluid connection between the at least one debris reservoir and the reserve.

* * * * *